United States Patent
Kahle

(10) Patent No.: US 9,585,598 B2
(45) Date of Patent: Mar. 7, 2017

(54) SYSTEM FOR DETERMINING POSITION IN A WORK SPACE

(71) Applicant: Trimble Navigation Limited, Sunnyvale, CA (US)

(72) Inventor: Kent Kahle, Sunnyvale, CA (US)

(73) Assignee: Trimble Inc., Sunnyvale, CA (US)

(*) Notice: Subject to any disclaimer, the term of this patent is extended or adjusted under 35 U.S.C. 154(b) by 0 days.

(21) Appl. No.: 13/657,347

(22) Filed: Oct. 22, 2012

(65) Prior Publication Data

US 2013/0147667 A1   Jun. 13, 2013

Related U.S. Application Data

(63) Continuation of application No. 12/634,055, filed on Dec. 9, 2009, now Pat. No. 8,319,687.

(51) Int. Cl.
  *G01S 5/14*   (2006.01)
  *G01C 15/00*  (2006.01)
  (Continued)

(52) U.S. Cl.
  CPC ............ *A61B 5/061* (2013.01); *G01C 15/002* (2013.01); *G01C 15/06* (2013.01); *G01S 5/0231* (2013.01);
  (Continued)

(58) Field of Classification Search
  CPC .. G01S 13/46; G01S 2013/466; G01S 5/0231; G01S 5/14; G01S 13/874;
  (Continued)

(56) References Cited

U.S. PATENT DOCUMENTS 5,299,130 A    3/1994 Ono
5,309,913 A *  5/1994 Kormos ............ A61B 17/3403
                                            600/429
(Continued)

FOREIGN PATENT DOCUMENTS

CA       2655805 A1 * 12/2007
DE  102006029122 A1   12/2007
(Continued)

OTHER PUBLICATIONS

B.W. Parkinson et al., Global Positioning System: Theory and Applications, vol. 1; Progress in Astronautics and Aeronatics, vol. 163, American Institute of Aeronautics and Astronautics, Inc., p. 10-12, 1996.*

(Continued)

*Primary Examiner* — Gregory C Issing
*Assistant Examiner* — Fred H Mull
(74) *Attorney, Agent, or Firm* — Kilpatrick Townsend & Stockton LLP

(57) ABSTRACT

A system for determining the dimensional coordinates of a point of interest in a work space, includes a plurality of fixed-position ranging radios, located at known positions in the work space, and a wand having a first end configured for indicating a point of interest. A pair of ranging radios are mounted on the wand. A measurement circuit, responsive to the pair of ranging radios, determines the position of each of the pair of ranging radios with respect to the plurality of fixed-position ranging radios, and determines the position of the first end of the wand with respect to the plurality of fixed position ranging radios. A robotic total station may be used in lieu of the fixed-position ranging radios to monitor the positions of retroreflective elements on the wand.

15 Claims, 4 Drawing Sheets

(51) Int. Cl.

| | |
|---|---|
| *G01C 15/06* | (2006.01) |
| *G01S 13/46* | (2006.01) |
| *G01S 13/87* | (2006.01) |
| *G01S 17/87* | (2006.01) |
| *A61B 5/06* | (2006.01) |
| *G01S 5/02* | (2010.01) |

(52) U.S. Cl.
CPC ............... *G01S 5/14* (2013.01); *G01S 13/46* (2013.01); *G01S 13/874* (2013.01); *G01S 13/878* (2013.01); *G01S 17/875* (2013.01); *G01S 2013/466* (2013.01)

(58) Field of Classification Search
CPC ..... G01S 13/878; G01S 17/875; G01C 15/02; G01C 15/06; G01C 15/002; A61B 2019/5251; A61B 5/06–5/061; A61B 5/064; A61B 5/065; G06F 3/0346; G06F 3/05345
USPC .................................. 342/453, 458, 463–465
See application file for complete search history.

(56) References Cited

U.S. PATENT DOCUMENTS

| | | | | |
|---|---|---|---|---|
| 5,359,521 | A | * | 10/1994 | Kyrtsos .................. G01S 19/47 340/988 |
| 5,510,800 | A | | 4/1996 | McEwan |
| 5,622,170 | A | * | 4/1997 | Schulz .................. A61B 5/0064 356/141.1 |
| 5,661,490 | A | | 8/1997 | McEwan |
| 5,663,734 | A | | 9/1997 | Krasner |
| 5,748,147 | A | | 5/1998 | Bickley et al. |
| 5,790,476 | A | * | 8/1998 | Stenstrom .................. E03F 7/00 367/120 |
| 5,901,172 | A | | 5/1999 | Fontana et al. |
| 5,903,235 | A | * | 5/1999 | Nichols .................. G01C 15/00 342/357.31 |
| 5,907,395 | A | * | 5/1999 | Schulz .................. G01B 11/002 356/139.03 |
| 5,960,413 | A | | 9/1999 | Amon et al. |
| 6,054,950 | A | | 4/2000 | Fontana |
| 6,377,839 | B1 | * | 4/2002 | Kalfas ................ A61B 17/3403 128/897 |
| 6,434,396 | B1 | * | 8/2002 | Rune ..................... H04W 68/10 455/502 |
| 6,535,282 | B2 | | 3/2003 | Hedges et al. |
| 6,812,884 | B2 | | 11/2004 | Richley et al. |
| 6,882,315 | B2 | | 4/2005 | Richley et al. |
| 6,963,301 | B2 | | 11/2005 | Schantz et al. |
| 6,975,959 | B2 | | 12/2005 | Dietrich et al. |
| 7,729,659 | B2 | | 6/2010 | Molisch et al. |
| 8,010,181 | B2 | * | 8/2011 | Smith ....................... A61B 5/06 600/411 |
| 8,319,687 | B2 | | 11/2012 | Kahle et al. |
| 8,355,888 | B2 | | 1/2013 | Chernoguz et al. |
| 8,663,204 | B2 | * | 3/2014 | Lechner ............... 606/1 |
| 8,862,200 | B2 | * | 10/2014 | Sherman .................. A61B 5/06 600/407 |
| 2002/0154294 | A1 | | 10/2002 | Hedges et al. |
| 2004/0012524 | A1 | * | 1/2004 | Couronne et al. ............ 342/387 |
| 2004/0107072 | A1 | | 6/2004 | Dietrich et al. |
| 2005/0113659 | A1 | * | 5/2005 | Pothier .................. A61B 90/36 600/372 |
| 2006/0089637 | A1 | * | 4/2006 | Werneth ............. A61B 18/1492 606/41 |
| 2006/0221864 | A1 | * | 10/2006 | Niu ........................ G01S 5/0289 370/255 |
| 2007/0139199 | A1 | * | 6/2007 | Hanlon ..................... G01S 5/02 340/572.1 |
| 2007/0293153 | A1 | | 12/2007 | Molisch et al. |
| 2008/0125630 | A1 | * | 5/2008 | Caylor .................. A61B 90/36 600/300 |
| 2008/0132911 | A1 | * | 6/2008 | Sobe ............................ 606/130 |
| 2008/0174409 | A1 | * | 7/2008 | Frank ................... A61B 5/6887 340/10.4 |
| 2009/0281419 | A1 | | 11/2009 | Troesken et al. |
| 2010/0004860 | A1 | * | 1/2010 | Chernoguz .......... G01C 22/006 701/494 |
| 2011/0054353 | A1 | * | 3/2011 | Hulvershorn .......... A61B 5/032 600/587 |

FOREIGN PATENT DOCUMENTS

| | | |
|---|---|---|
| DE | 112006003390 T5 | 10/2008 |
| DE | 102008059365 A1 | 6/2010 |

OTHER PUBLICATIONS

K.W. Kolodziej et al., Local Positioning Systems: LBS Applications and Services, p. 147-148, CRC Press, 2006.*
E. Doukhnitch et al., An efficient approach for trilateration in 3D positioning, Computer Communications vol. 31(17). p. 4124-4129, 2008.*
Fontana et al., "A Programmable Ultra Wideband Signal Generator for Electromagnetic Susceptibility Testing", IEEE Conference on Ultra Wideband Systems and Technologies, Nov. 2003, Reston, VA.
Fontana et al., "Commercialization of an Ultra Wideband Precision Asset Location System", IEEE Conference on Ultra Wideband Systems and Technologies, Nov. 2003, Reston, VA.
Fontana, "Current Trends in UWB Systems in the USA, Implementation, Applications and Regulatory Issues", Multispectral Solutions, Inc., Advanced Ratio Technology Symposium, 2002, Tokyo, Japan.
Fontana, "On 'Range-Bandwidth per Joule' for Ultra Wideband and Spread Spectrum Waveforms", Multispectral Solutions, Inc., Mar. 20, 1998.
Bennett et al., "Time-Domain Electromagnetics and Its Applications", Proceedings of the IEEE, vol. 66, No. 3, Mar. 1978.
Fontana, "Recent System Applications of Short-Pulse Ultra-Wideband (UWB) Technology", IEEE Microwave Theory and Tech., vol. 52, No. 9, Sep. 2004.
Fontana et al., "Ultra-Wideband Precision Asset Location", 2002 IEEE Conference on Ultra Wideband Systems and Technologies, May 2002, Baltimore, MD.
Fontana et al., "Ultra Wideband Technology for Aircraft Wireless Intercommunications Systems (AWICS) Design", 2003 IEEE Conference on Ultra Wideband Systems and Technologies, Nov. 2003, Reston, VA.
Office Action dated Mar. 19, 2012 pertaining to German Application No. 10 2010 037 739.2.
Office Action dated Oct. 24, 2012 pertaining to China Application No. 201010586093.2.

* cited by examiner

SYSTEM FOR DETERMINING POSITION IN A WORK SPACE

CROSS-REFERENCE TO RELATED APPLICATION

This application is a continuation of U.S. patent application Ser. No. 12/634,055 filed Dec. 9, 2009.

STATEMENT REGARDING FEDERALLY SPONSORED RESEARCH OR DEVELOPMENT

Not applicable.

BACKGROUND OF THE INVENTION

This relates to a system for facilitating spatial positioning including a work space or work site, such as for example a construction site or elsewhere. For example, when the interior of a building is being finished, there is a need to determine the location of various interior features, such as the proper location of walls, windows, and doors. There are a large number of electrical, plumbing, and HVAC components that must be properly sited. Further, beams, joists, ceilings, tiles, shelves, cabinets, and other similar components that must be accurately positioned. After the construction of the interior of the building begins, positioning of various components must be accomplished quickly and with some precision with respect to the surrounding walls, ceilings and floors as they are roughed in. Typically, it has required a significant amount of labor to lay out construction points at a construction site. Teams of workers have been needed to measure and mark various locations. It will be appreciated that this process has been subject to errors, both from measurement mistakes and from accumulated errors which compound as measurements are made from one intermediate point to another. A number of tools have been developed to facilitate this process, although many of these tools are somewhat complicated to use, and require careful attention to achieve the desired accuracy.

Ranging radios offer an excellent alternative to GPS receivers for positioning applications where GPS reception is not available, such as inside a building, or where use of GPS receivers is not reliable. For example, GPS receivers require line-of-sight access to multiple satellites in order to function properly. This may not be possible in some operational settings, such as when work is being performed indoors, underground, or in cluttered environments.

Ranging radios, operating at ultra wideband (UWB) frequencies, provide very accurate measurement of distances between the radios, using time-of-flight analysis. When ranging is accomplished from multiple fixed position radios to a target radio, the relative, three-dimensional position of the target radio is accomplished through trilateration. To perform a range measurement, an originating ranging radio transmits a packet consisting of a synchronization preamble and a header. The header contains the range command with the address of the destination radio that is requested to respond to the packet. The originating radio resets its main counter at the time of this transmission, establishing a local time-zero reference. When the destination ranging radio receives the range request addressed to it, it records the time of receipt, and replies with its own packet, including the time of receipt and the time of the responding transmission in the header. The originating radio receives the ranging packet back from the destination radio, records its time of receipt and latches its main counter. The range value is then calculated and recorded, utilizing the time information to compensate for the differences in the timing clocks at the two radios.

It is desirable to provide an improved system using ranging radios to determine various positions at a work site. A difficulty arises, however, in that a ranging radio may not operate properly throughout a work site, especially if positioned close to a metal surface or beam, or completely or partially shielded from the fixed, reference ranging radios. Further, it is sometimes desirable to be able to determine the position of a point that is not easily accessible.

SUMMARY OF THE INVENTION

A system for determining the dimensional coordinates of a point of interest in a work space, includes a plurality of fixed position ranging radios located at known positions in the work space, and a wand having a first end configured for indicating a point of interest. A pair of ranging radios are mounted on the wand. A first ranging radio mounted on the wand is spaced from the first end of the wand by a first distance, and a second ranging radio mounted on the wand is spaced from the first ranging radio by a second distance. A measurement circuit, responsive to the pair of ranging radios, determines the position of each of the pair of ranging radios with respect to the plurality of fixed position ranging radios. The measurement circuit determines the position of the first end of the wand with respect to the plurality of fixed position ranging radios.

The first and second distances may be substantially equal. The wand may include a handle portion to facilitate the use of the wand by a user. The plurality of fixed position ranging radios may comprise at least four ranging radios. The wand may further include a marking element at the first end for marking on a surface. A display is responsive to the measurement circuit for indicating to a user the location of the first end of the wand. The measurement circuit may be responsive to a user input to permit the user to specify a desired position for the first end of the wand. The system may further comprise a display, responsive to the measurement circuit, for indicating the movement of the wand needed to move the first end of the wand to the desired position.

A system for determining the dimensional coordinates of a point of interest in a work space includes a device for measuring the positions of reference elements in the work space, and a wand having a first end configured for indicating a point of interest. A pair of reference elements is mounted on the wand. The first reference element is spaced from the first end of the wand by a first distance, and the second reference element is spaced from the first reference element by a second distance. A measurement circuit determines the position of the first end of the wand in the work space based on the positions of the pair of reference elements in the workplace.

The first and second distances may be substantially equal. The wand may include a handle portion to facilitate the use of the wand by a user. The device for measuring the positions of the reference elements may comprise a robotic total station. The reference elements may comprise autoreflective elements. The wand may further include a marking element at the first end for marking on a surface. The system may further comprise a display, responsive to the measurement circuit, for indicating to a user the location of the first end of the wand. The measurement circuit is responsive to a user input to permit the user to specify a desired position for the first end of the wand. The system further includes a display, responsive to the measurement circuit, for indicating the movement of the wand needed to move the first end of the wand to the desired position. The robotic total station may dither between the two auto-reflective elements so as to determine the positions of the two auto-reflective elements.

DETAILED DESCRIPTION OF THE PREFERRED EMBODIMENTS

Figure 1:
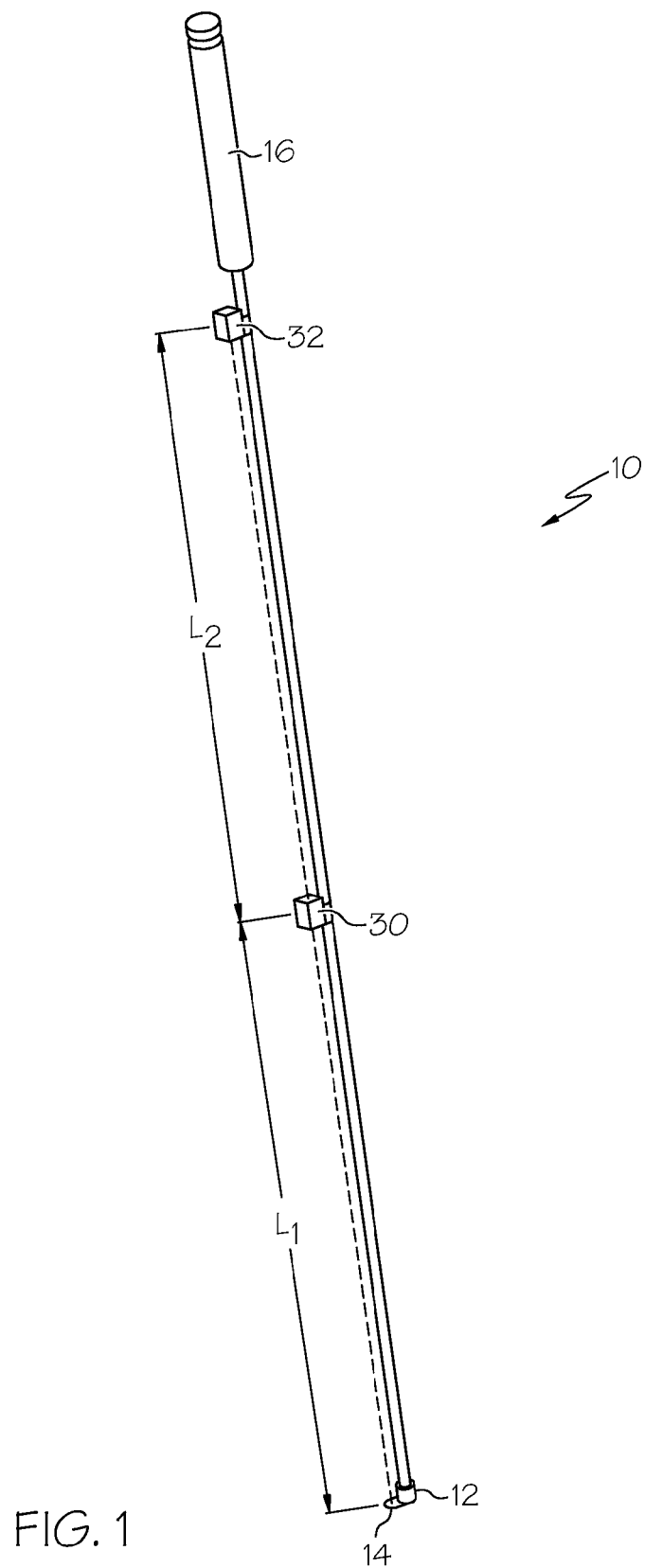
FIG. 1 shows a first embodiment of the wand and the pair of ranging radios mounted on the wand.
Figure 2:
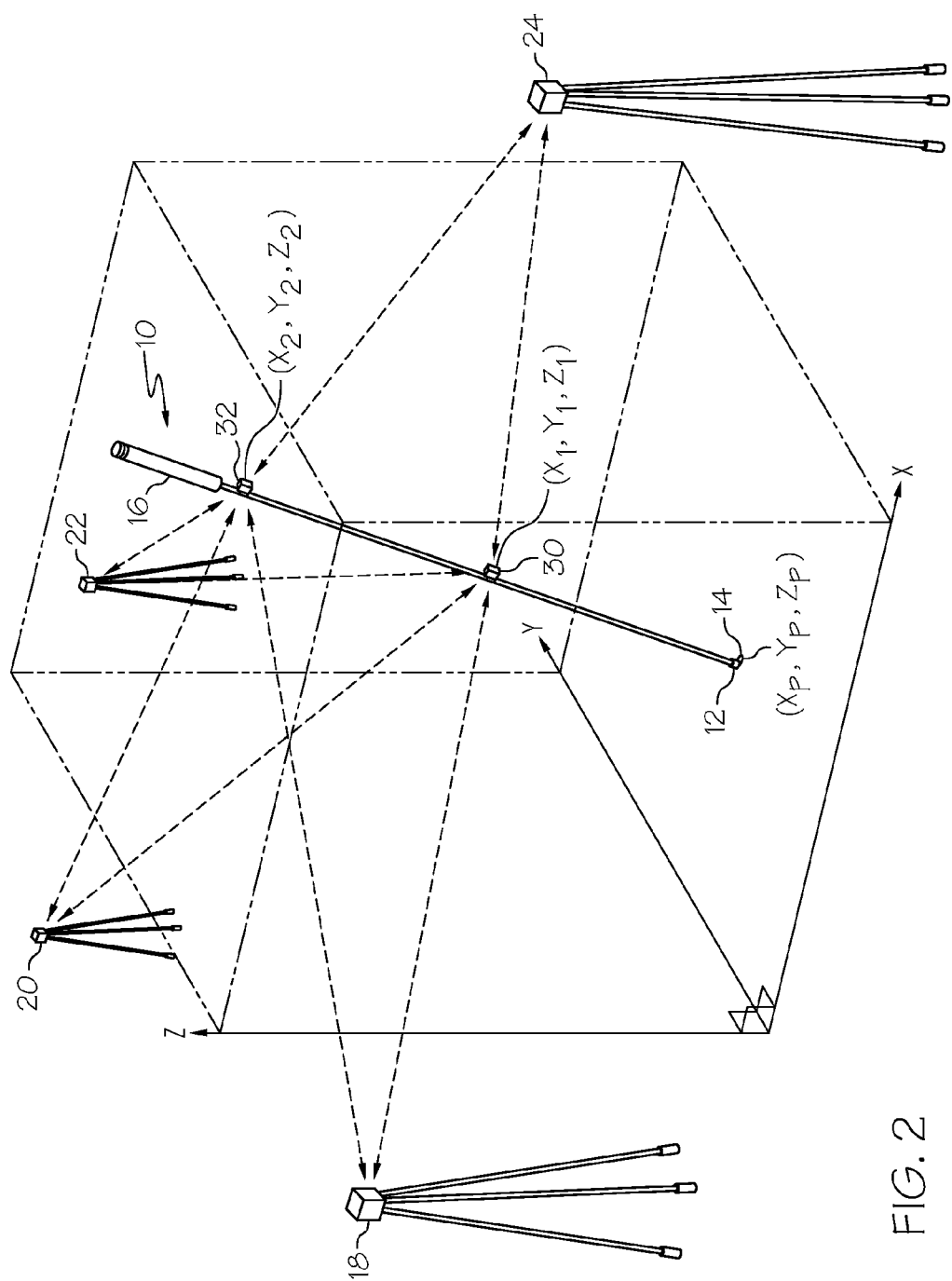
FIG. 2 is a diagrammatic view of the wand of FIG. 1, being used with four fixed-position ranging radios.
Figure 3:
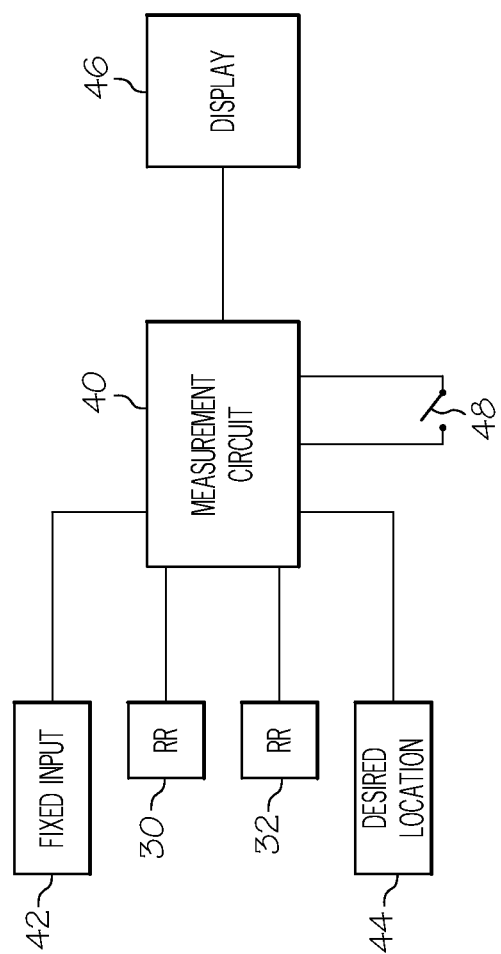
FIG. 3 is a schematic diagram of circuitry used in the system.

FIGS. 1-3 collectively illustrate a first embodiment of the system for determining the three dimensional coordinates of a point of interest in a work space. The system includes a wand 10 having a first end 12 configured to indicate a point of interest. The first end 12 may have a pointer element 14 that extends from the wand 10, as shown in FIG. 1. The wand 10 may further include a handle portion 16 to facilitate the use of the wand 10 by a user. As will be explained more fully, below, a user holds the wand 10 by handle portion 16 and manually positions the first end 12 of the wand so that the pointer element 14 is located at a point of interest. For example, the pointer element 14 may be touched to a point on a floor, wall, or ceiling so that the three-dimensional coordinates of that point can be determined.

The system further includes a plurality of fixed position ranging radios 18, 20, 22 and 24 (FIG. 2) which are located at known positions at the work space. These positions can be determined through any known surveying or measurement technique. Since the point of interest locations throughout the work space are determined from trilateration calculations with respect to the fixed position ranging radios, it is preferable that these fixed position ranging radios be widely dispersed at the work space to optimize accuracy. Trilateration is a method for determining the intersections of four spherical surfaces, given the locations of the centers and the length of the four spheres. In the present case, the locations of the fixed position ranging radios define the centers of four spheres, and the distance from each ranging radio to a movable ranging radio defines the radius of each sphere. When the distance from a fixed ranging radio to a point of interest is known, the point of interest will necessarily lie somewhere on a spherical surface having a center at the ranging radio, and having a radius equal to the distance. If such distances are determined with respect to all four of the ranging radios, the spherical surfaces that are defined will intersect at the point of interest. Accurate position determination for each of the fixed position ranging radios 18, 20, 22 and 24 is therefore important for accurate operation of the system.

A pair of ranging radios is mounted on the wand 10. A first ranging radio 30 is spaced from the first end 12 by a first distance $L_1$, and a second ranging radio 32 is spaced from the first ranging radio 30 by a second distance $L_2$.

Reference is made to FIG. 2, in which the coordinates of ranging radio 30 are $X_1$, $Y_1$, and $Z_1$, the coordinates of ranging radio 32 are $X_2$, $Y_2$, and $Z_2$, and the coordinates of pointer element 14 at the end 12 of the wand 10 are $X_P$, $Y_P$, and $Z_P$. Ranging radios 30 and 32 lie on a common line with pointer element 14, as indicated by the dashed line in FIG. 1. It will be apparent from a review of FIG. 2, that $(X_2-X_1)/L_2=(X_1-X_P)/L_1$ and $X_P=X_1+(L_1/L_2)(X_1-X_2)$.

Similarly, $Y_P=Y_1+(L_1/L_2)(Y_1-Y_2)$, and $Z_P=Z_1+(L_1/L_2)(Z_1-Z_2)$.

If $L_1=L_2$, then these relationships simplify even further to $X_P=2X_1-X_2$, $Y_P=2Y_1-Y_2$, and $Z_P=2Z_1-Z_2$.

Thus, if the three-dimensional coordinates of the two ranging radios 30 and 32 are determined, the three-dimensional coordinates of the pointer element 14 is also known. The coordinates of ranging radios 30 and 32 are determined by use of the fixed position ranging radios 18, 20, 22 and 24, as described below.

The system further includes a measurement circuit 40 (FIG. 3) which is responsive to the pair of ranging radios 30 and 32. Circuit 40 determines the position of each of the ranging radios 30 and 32 with respect to the plurality of fixed position ranging radios 18, 20, 22, and 24 using trilateration analysis. The circuit 40 then determines the three-dimensional coordinates of the first end 12 and, more specifically, the three-dimensional coordinates of the pointer element 14, with respect to the plurality of fixed position ranging radios 18, 20, 22, and 24. The measurement circuit 40 receives the coordinates of the ranging radios 18, 20, 22, and 24 through a manual input at 42, or by any other appropriate means. As will also be noted in FIG. 3, an input 44 is also provided for inputting a desired position. An operator display 46 is responsive to the measurement circuit 40. The components of FIG. 3 may be integral with the wand 10, or may be packaged separately, and carried separately by the user of the system. Further, the ranging radios 30 and 32 are shown in FIG. 3 as being directly connected to the measurement circuit 40, but may alternatively be connected via a radio link, or other wireless link.

In use, the fixed ranging radios 18, 20, 22, and 24 are positioned at the work place, and their three-dimensional coordinates noted and provided to circuit 40 via 42. As is known, to insure that ambiguities are eliminated, the fixed ranging radios are located so that they are not all in the same plane. The wand 10 is then moved by the operator so that the pointer element 12 is touching a point of interest, the coordinates of which are to be determined. When the wand 20 is properly positioned, this is signaled by the operator momentarily closing switch 48, which may be a switch on the wand 10, or a switch located elsewhere with the measurement circuit. At this instant, the coordinates of the pointer element 14, $X_P$, $Y_P$, and $Z_P$, are determined and stored. The locations of additional points may be taken and stored in the same manner. It is also possible to use the system to locate a point, the three-dimensional coordinates of which have been previously determined. To accomplish this, the desired location is input at 44. The operator then monitors the display 46 as the wand 10 is moved, with the display providing an indication of which direction and by what distance the pointer element 14 must be moved in order for it to reach the desired location. If desired, the pointer element 14 may be configured as a small wire loop to which a felt-tip marker or other marking device can be secured. By this arrangement, the wand may be moved to a predetermined position, and a mark made on a surface at that predetermined position.

It will be appreciated that using four fixed position ranging radios at known positions, but not located in a common plane, permits point of interest locations throughout the work space to be determined unambiguously with trilateration calculations. It will also be appreciated that if only three fixed position ranging radios at known positions are used, the ambiguity which results is that the point of interest may be at either of two possible locations. The two possible locations will be located above and below a plane which is common to the three fixed position ranging radios. If one of the two possible locations can be eliminated in some manner, then the ambiguity is eliminated and only three fixed position ranging radios are required for operation of the system. As an example, the ambiguity can be eliminated by situating the three fixed position ranging radios on the floor of an interior work site. The point of interest will always be above the floor level, and will therefore always be above the level of the common plane. The possible three dimensional coordinate with the higher Z dimension coordinate will be therefore always be selected as the point of interest location.

If desired, a system may be configured to determine the coordinates of a point of interest in two dimensional space. Such a two dimensional system could be used, for example, to lay out positions for equipment or structures on the floor of a building. In order to accomplish two dimensional layout, only two fixed position ranging radios need be used. As discussed, above, a system with three fixed position ranging radios will provide an ambiguous solution to the location calculation in that the point of interest could be at either of two positions, one position below the plane of the fixed position ranging radios, and the other position above the plane of the fixed position ranging radios. With only two fixed position ranging radios, the ambiguity is increased, with the position of interest being found to lie somewhere on a circle. The circle will be oriented such that it is a first uniform distance from a first of the radios and a second uniform distance from the second of the radios, with the first and second uniform distances being not necessarily equal. If the fixed position ranging radios are located on the floor of the work site, and if the point of interest is constrained to lie somewhere on the floor, then the ambiguity reduces to one of two possible points on the floor. Further, if the two ranging radios are placed on the floor at the side of the room such that one of the two points can be eliminated as being outside the room, then the ambiguities are eliminated, and a two dimensional layout on the floor of the work site can be accomplished.

Figure 4:
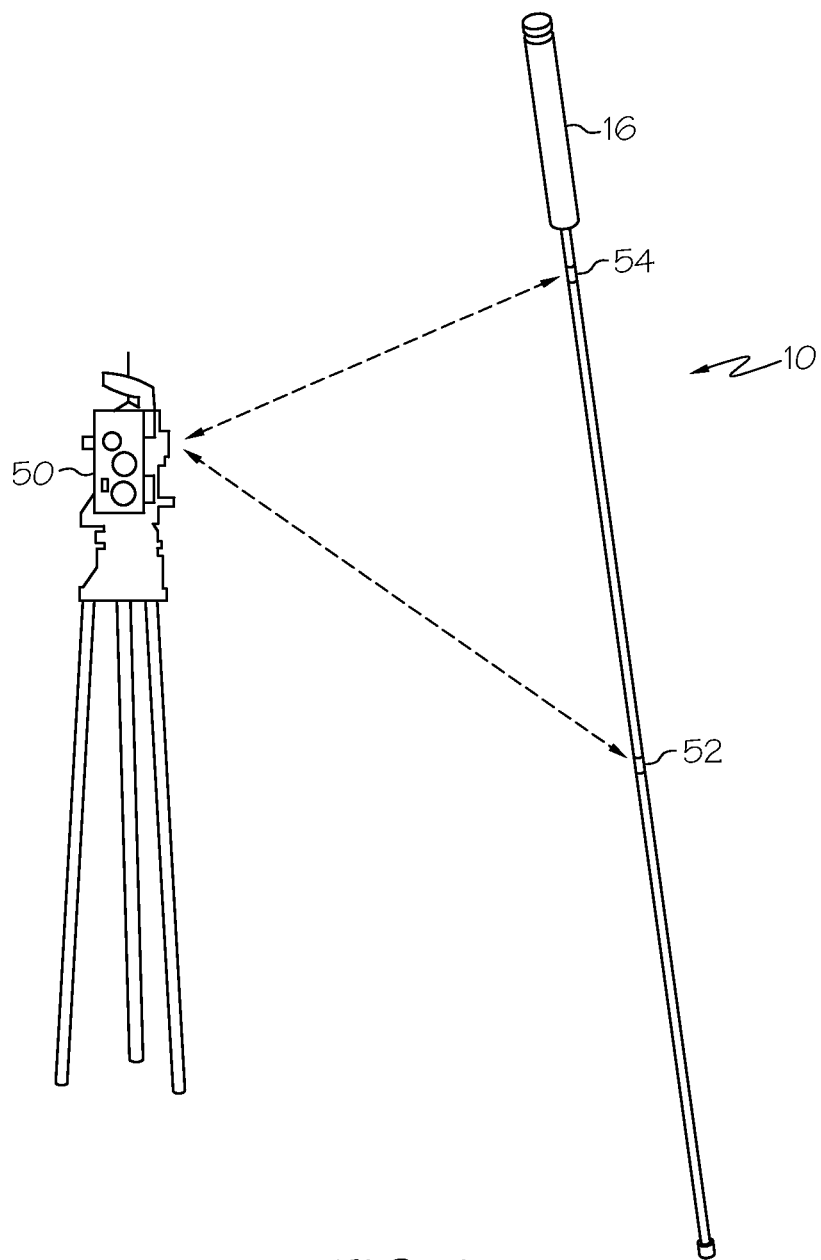
FIG. 4 shows a second embodiment of the wand having retroreflective elements in use with a robotic total station.

FIG. 4 illustrates another embodiment of the invention which includes a device, such as a robotic total station 50, for measuring the positions of reference elements 52 and 54 on the wand 10. The robotic total station is a device of the type available from Trimble Navigation Limited, which tracks one or more autoreflective elements and provides a continuous stream of data on the positions of such elements. The reference elements 52 and 54 in this embodiment consist of small bands of retroreflective tape that are wrapped around the wand 10 in the same relative positions as described above with respect to the ranging radios 30 and 32 in the first embodiment. The robotic total station repeatedly directs a thin beam of laser light to each of the reference elements 52 and 54, dithering between the elements. The total station receives the reflected light, and measures the time of flight of the beam. From this data, the measurement circuit 40 in the robotic total station 50 is able to calculate the three-dimensional coordinates of the elements 52 and 54, and the position of the tip 12 is therefore precisely specified. It will be appreciated that retroreflective cubes or other devices may be used instead of the tape strips 52 and 54.

Although particular embodiments have been described above for purposes of illustration, it will be appreciated by those skilled in the art that numerous variations in these embodiments may be made.

What is claimed is:

1. A system for determining the dimensional coordinates of a point of interest in a work space, the system comprising:
   four or more fixed position ranging radios located at known positions in the work space, said four or more fixed position ranging radios defining four or more spheres in a workplace, wherein said four or more fixed position ranging radios are not in a same plane, and wherein each of the four or more fixed position ranging radios is configured to transmit a locating signal;
   a wand, comprising:
      a first end configured to indicate the point of interest, wherein the point of interest is external to the wand,
      first and second ranging radios, wherein the first ranging radio is spaced from said first end by a first distance, wherein the second ranging radio spaced from said first ranging radio by a second distance, and wherein each of the first and second ranging radios is configured to receive the locating signals from the fixed position ranging radios, and
      a measurement circuit electrically connected with the first and second ranging radios, said measurement circuit configured to determine the position of each of the first and second ranging radios with respect to said plurality of fixed position ranging radios using signals generated by the first and second ranging radios, wherein said measurement circuit is configured to receive a signal indicating that the first end of the wand is positioned at the point of interest, wherein said measurement circuit is configured to, in response to the received signal, determine the three dimensional position of said first end of said wand with respect to said plurality of fixed position ranging radios, and wherein the three dimensional position of said first end of said wand is determined as an indication of the three dimensional position of the point of interest; and
   a display, wherein the display is configured to provide information based on the position of each of the first and second ranging radios.

2. The system of claim 1, in which said wand further includes a handle portion to facilitate the use of said wand by a user.

3. The system of claim 1, in which said wand further includes a marking element at said first end to mark a surface.

4. The system of claim 1, wherein the display is configured to indicate to a user the location of said first end of said wand.

5. The system of claim 1, in which said measurement circuit is responsive to a user input to permit said user to specify a desired position for said first end of said wand, and wherein the display is configured to indicate the movement of said wand needed to move said first end of said wand to said desired position.

6. A method to determine the dimensional coordinates of a point of interest in a work space, the method comprising:

receiving at a first ranging radio, four or more first ranging distance signals corresponding to first distances between said first ranging radio and four or more fixed position ranging radios, said four or more fixed position ranging radios being located at known positions in the work space, said four or more fixed position ranging radios defining four or more spheres in a workspace, wherein said four or more fixed position ranging radios are not in a same plane;

receiving at a second ranging radio, a plurality of second ranging distance signals corresponding to second distances between said second ranging radio and said four or more fixed position ranging radios;

receiving a signal indicating that a first end of a wand is positioned at the point of interest, wherein the point of interest is external to the wand;

determining with a measurement circuit local to said first ranging radio and said second ranging radio, a first position of said first ranging radio in a workspace from the plurality of first ranging distances and a second position of said second ranging radio in said workspace from the plurality of second ranging distances using said signals indicating said first and second distances received by said first and second ranging radios;

in response to the received signal, determining coordinates of the point of interest in the work space, said wand comprising:

said first ranging radio and said second ranging radio mounted on said wand, said first ranging radio and said second ranging radio both spaced from said first end, said first ranging radio spaced from said first end by a first distance, and said second ranging radio spaced from said first ranging radio by a second distance, and said measurement circuit, configured to determine the three dimensional position of said first end of said wand with respect to said first position of said first ranging radio and said second position of said second ranging radio, wherein said measurement circuit is configured to receive the signal indicating that the first end of the wand is positioned at the point of interest, wherein said measurement circuit is configured to, in response to the received signal, determine the coordinates of the first end of said wand, and wherein the coordinates of said first end of the wand is determined as an indication of the coordinates of the point of interest; and displaying on a display, information based on the position of each of the first and second ranging radios.

7. The method of claim 6, further comprising receiving an input specifying a desired position for said first end of said wand, wherein the display is configured to indicate a movement of said wand needed to move said first end of said wand to said desired position.

8. The method of claim 7, further comprising indicating on the display said point of interest and marking said point of interest using a marking element at said first end.

9. The method of claim 6, wherein the display is configured to indicate to a user the location of said first end of said wand.

10. The method of claim 6, wherein said wand further includes a handle portion to facilitate the use of said wand by a user.

11. A method of determining the dimensional coordinates of a point of interest in a work space, the method comprising:

communicating with four or more fixed position ranging radios located at known positions in the work space with a measurement circuit, said four or more fixed position ranging radios defining four or more spheres in a workplace, wherein said four or more fixed position ranging radios are not in a same plane;

receiving a signal indicating that a first end of a wand is positioned at the point of interest, wherein the point of interest is external to the wand;

in response to the received signal, calculating with said measurement circuit, the three-dimensional coordinates of the point of interest with respect to said four or more fixed position ranging radios using trilateration analysis, said wand comprising:

a pair of ranging radios spaced from said first end, a first ranging radio spaced from said first end by a first distance, and a second ranging radio spaced from said first ranging radio by a second distance, the first and second ranging radios each configured to receive location signals from the four or more fixed position ranging radios; and said measurement circuit, responsive to said pair of ranging radios, and configured to determine the three dimensional position of each of said pair of ranging radios with respect to said four or more fixed position ranging radios, and, in response to receiving the signal indicating that a first end of the wand is positioned at the point of interest, to determine the position of said first end with respect to said four or more fixed position ranging radios using signals generated by said pair of ranging radios, and wherein the three-dimensional coordinates of said first end of the wand is determined as the three-dimensional coordinates of the point of interest;

displaying on a display, information based on the position of each of the ranging radios of the pair of ranging radios; and storing said three-dimensional coordinates of said point of interest.

12. The method of claim 11, further comprising displaying the location of said point of interest on the display.

13. The method of claim 12, further comprising indicating said point of interest to mark with a marking element at said first end.

14. The method of claim 11, further comprising:

locating a desired location, wherein said desired location is input into said measurement circuit; and displaying a movement said wand is needed to move said pointer element to indicate said desired location on the display.

15. The method of claim 11, wherein said wand further includes a handle portion to facilitate the use of said wand by a user.

* * * * *